US006797510B1

(12) United States Patent
Walke et al.

(10) Patent No.: US 6,797,510 B1
(45) Date of Patent: Sep. 28, 2004

(54) HUMAN KINASES AND POLYNUCLEOTIDES ENCODING THE SAME

(75) Inventors: D. Wade Walke, Spring, TX (US); John Scoville, Houston, TX (US); Carl Johan Friddle, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 124 days.

(21) Appl. No.: 10/196,927

(22) Filed: May 20, 2002

Related U.S. Application Data

(60) Provisional application No. 60/293,248, filed on May 24, 2001.

(51) Int. Cl.$^7$ .......................... C12N 1/20; C12N 15/00; C12N 5/00; C12Q 1/68; C07H 21/04
(52) U.S. Cl. .......................... 435/252.3; 435/194; 435/6; 435/320.1; 435/325; 536/23.2
(58) Field of Search .......................... 435/252.3, 320.1, 435/6, 325, 194; 536/23.2

(56) References Cited

U.S. PATENT DOCUMENTS

| | | | |
|---|---|---|---|
| 4,215,051 A | 7/1980 | Schroeder et al. | 260/346.7 |
| 4,376,110 A | 3/1983 | David et al. | 430/513 |
| 4,594,595 A | 6/1986 | Struckman | 343/770 |
| 4,631,211 A | 12/1986 | Houghten | 428/35 |
| 4,689,405 A | 8/1987 | Frank et al. | 536/27 |
| 4,713,326 A | 12/1987 | Dattagupta et al. | 435/6 |
| 4,873,191 A | 10/1989 | Wagner et al. | 435/172.3 |
| 4,946,778 A | 8/1990 | Ladner et al. | 435/69.6 |
| 5,252,743 A | 10/1993 | Barrett et al. | 548/303.7 |
| 5,272,057 A | 12/1993 | Smulson et al. | 435/6 |
| 5,424,186 A | 6/1995 | Fodor et al. | 435/6 |
| 5,445,934 A | 8/1995 | Fodor et al. | 435/6 |
| 5,459,127 A | 10/1995 | Felgner et al. | 514/7 |
| 5,556,752 A | 9/1996 | Lockhart et al. | 435/6 |
| 5,700,637 A | 12/1997 | Southern | 435/6 |
| 5,723,323 A | 3/1998 | Kauffman et al. | 435/172.3 |
| 5,744,305 A | 4/1998 | Fodor et al. | 435/6 |
| 5,756,289 A | 5/1998 | Hoekstra | 435/6 |
| 5,817,479 A | 10/1998 | Au-Young et al. | 435/69.1 |
| 5,830,721 A | 11/1998 | Stemmer et al. | 435/172.1 |
| 5,837,458 A | 11/1998 | Minshull et al. | 435/6 |
| 5,869,336 A | 2/1999 | Meyer et al. | 435/348 |
| 5,877,397 A | 3/1999 | Lonberg et al. | 800/2 |
| 5,948,767 A | 9/1999 | Scheule et al. | 514/44 |
| 6,075,181 A | 6/2000 | Kucherlapati et al. | 800/25 |
| 6,110,490 A | 8/2000 | Thierry | 424/450 |
| 6,114,598 A | 9/2000 | Kucherlapati et al. | 800/18 |
| 6,117,679 A | 9/2000 | Stemmer | 435/440 |
| 6,150,584 A | 11/2000 | Kucherlapati et al. | 800/18 |
| 6,340,583 B1 | 1/2002 | Yan et al. | 435/194 |

OTHER PUBLICATIONS

Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IVα–anomeric and β–anomeric tetrathymidylates covalently linked to intercalating oxazolopyridocarbazole. Synthesis, physiochemical properties and poly (rA) binding", Nucleic Acids Research 15(16):6625–6641.
Gordon, 1989, "Transgenic Animals", International Review of Cytology, 115:171–229.
Greenspan et al, 1993, "Idiotypes: structure and immunogenicity", FASEB Journal 7:437–444.
Gu et al, 1994, "Deletion of a DNA Polymerase β Gene Segment in T Cells Using Cell Type–Specific Gene Targeting", Science 265:103–106.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985, "Up–promoter mutations in the lpp gene of *Escherichia coli*", Nucleic Acids Research 13(9):3101–3110.
Janknecht et al, 1991, "Rapid and efficient purification of native histidine–tagged protein expressed by recombinant vaccinia virus", PNAS 88:8972–8976.
Kohler & Milstein, 1975, "Continuous cultures of fused cells secreting antibody of predefined specificity", Nature 256:495–497.
Lakso et al, 1992, "Targeted oncogene activation by site–specific recombination in transgenic mice", Proc. Natl. Acad. Sci. USA 89:6232–6236.
Lavitrano et al, 1989, "Sperm Cells as Vectors for Introducing Foreign DNA into Eggs: Genetic Transformation of Mice", Cell 57:717–723.
Lo, 1983, "Transformation by Iontophoretic Microinjection of DNA: Multiple Integrations without Tandem Insertions", Mol. & Cell. Biology 3(10):1803–1814.
Logan et al, 1984, "Adenovirus tripartite leader sequence enhances translation of mRNAs late after infection", Proc. Natl. Acad. Sci. USA 81:3655–3659.
Lowy et al, 1980, "Isolation of Transforming DNA: Cloning the Hamster aprt Gene", Cell 22:817–823.

(List continued on next page.)

*Primary Examiner*—Maryam Monshipouri

(57) ABSTRACT

Novel human polynucleotide and polypeptide sequences are disclosed that be used in therapeutic, diagnostic, and pharmacogenomic applications.

5 Claims, No Drawings

OTHER PUBLICATIONS

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications," J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the polyhedrin Gene", J. Virol. 46(2):584–593.

Stein et al, 1988, "Physiochemical properties of phosphorothioate oligodeoxynucleotides", Nucleic Acids Research 16(8):3209–3221.

Takeda et al, 1985, "Construction of chimaeric processed immunoglobulin genes containing mouse variable and human constant region sequences", Nature 314:452–454.

Thompson et al, 1989, "Germ Line Transmission and Expression of a Corrected HPRT Gene Produced by Gene Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammalian cells with an amplifiable dominant–acting gene", Proc. Natl. Acad. Sci. USA 77(6):3567–3570.

SEQUENCE LISTING

<160> NUMBER OF SEQ ID NOS: 5

<210> SEQ ID NO 1
<211> LENGTH: 1938
<212> TYPE: DNA
<213> ORGANISM: homo sapiens

<400> SEQUENCE: 1

```
atgctgaaat tccaagaggc agctaagtgt gtgagtggat caacagccat ttccacttat      60
ccaaagacct tgattgcaag aagatacgtg cttcaacaaa aacttggcag tggaagtttt     120
ggaactgtct atctggtttc agacaagaaa gccaaacgag gagaggaatt aaaggtactt     180
aaggaaatat ctgttggaga actaaatcca aatgaaactg tacaggccaa tttggaagcc     240
caactcctct ccaagctgga ccacccagcc attgtcaagt tccatgcaag ttttgtggag     300
caagataatt tctgcattat cacggagtac tgtgagggcc gagatctgga cgataaaatt     360
caggaatata aacaagctgg aaaaatcttt ccagaaaatc aaataataga atggtttatc     420
cagctgctgc tgggagttga ctacatgcat gagaggagga tacttcatcg agacttaaag     480
tcaaagaatg tatttctgaa aaataatctc cttaaaattg gagattttgg agtttctcga    540
```

```
cttctaatgg gatcctgtga cctggccaca actttaactg gaactcccca ttatatgagt      600
cctgaggctc tgaaacacca aggctatgac acaaagtcgg acatctggtc actggcatgc      660
attttgtatg agatgtgctg catgaatcat gcattcgctg gctccaattt cttatccatt      720
gttttaaaaa ttgttgaagg tgacacacct tctctccctg agagatatcc aaaagaacta      780
aatgccatca tggaaagcat gttgaacaag aatccttcat taagaccatc tgctatcgaa      840
attttaaaaa tcccttacct tgatgagcag ctacagaacc taatgtgtag atattcagaa      900
atgactctgg aagacaaaaa tttggattgt cagaaggagg ctgctcatat aattaatgcc      960
atgcaaaaaa ggatccacct gcagactctg agggcactgt cagaagtaca gaaaatgacg     1020
ccaagagaaa ggatgcggct gaggaagctc caggcggctg atgagaaagc caggaagctg     1080
aaaaagattg tggaagaaaa atatgaagaa aatagcaaac gaatgcaaga attgagatct     1140
cggaactttc agcagctgag tgttgatgta ctccatgaaa aaacacattt aaaaggaatg     1200
gaagaaaagg aggagcaacc tgagggaaga ctttcttgtt caccccagga cgaggatgaa     1260
gagaggtggc aaggcaggga agaggaatct gatgaaccaa ctttagagaa cctgcctgag     1320
tctcagccta ttccttccat ggacctccac gaacttgaat caattgtaga ggatgccaca     1380
tctgaccttg gataccatga gatcccagaa gacccacttg tggctgaaga gtactacgct     1440
gatgcatttg attcctattg tgtagagagt gatgaggagg aagaagaaat agcgttagaa     1500
agaccagaga aagaaatcag gaatgaggga tcccagcctg cttacagaac aaaccaacag     1560
gacagtgata tcgaagcgtt ggccaggtgt ttggaaaatg tcctgggttg cacttctcta     1620
gacacaaaga ccatcaccac catggctgaa gacatgtccc caggaccacc aattttcaac     1680
agtgtgatgg ccaggaccaa gatgaaacgc atgagggaat cagccatgca gaagctgggg     1740
acagaagtat ttgaagaggt ctataattac ctcaagagag caaggcatca gaatgctagc     1800
gaagcagaga tccgcgagtg tttggaaaaa gtggtgcctc aagccagcga ctgttttgaa     1860
gtggaccagc tcctgtactt tgaagagcag ttgctgatca cgatgggaaa agaacctact     1920
ctccagaacc atctctag                                                  1938
```

<210> SEQ ID NO 2
<211> LENGTH: 645
<212> TYPE: PRT
<213> ORGANISM: homo sapiens

<400> SEQUENCE: 2

```
Met Leu Lys Phe Gln Glu Ala Ala Lys Cys Val Ser Gly Ser Thr Ala
  1               5                  10                  15

Ile Ser Thr Tyr Pro Lys Thr Leu Ile Ala Arg Arg Tyr Val Leu Gln
             20                  25                  30

Gln Lys Leu Gly Ser Gly Ser Phe Gly Thr Val Tyr Leu Val Ser Asp
         35                  40                  45

Lys Lys Ala Lys Arg Gly Glu Glu Leu Lys Val Leu Lys Glu Ile Ser
     50                  55                  60

Val Gly Glu Leu Asn Pro Asn Glu Thr Val Gln Ala Asn Leu Glu Ala
 65                  70                  75                  80

Gln Leu Leu Ser Lys Leu Asp His Pro Ala Ile Val Lys Phe His Ala
                 85                  90                  95

Ser Phe Val Glu Gln Asp Asn Phe Cys Ile Ile Thr Glu Tyr Cys Glu
            100                 105                 110

Gly Arg Asp Leu Asp Asp Lys Ile Gln Glu Tyr Lys Gln Ala Gly Lys
```

-continued

```
            115                 120                 125
Ile Phe Pro Glu Asn Gln Ile Ile Glu Trp Phe Ile Gln Leu Leu
        130                 135                 140
Gly Val Asp Tyr Met His Glu Arg Arg Ile Leu His Arg Asp Leu Lys
145                 150                 155                 160
Ser Lys Asn Val Phe Leu Lys Asn Asn Leu Leu Lys Ile Gly Asp Phe
                165                 170                 175
Gly Val Ser Arg Leu Leu Met Gly Ser Cys Asp Leu Ala Thr Thr Leu
                180                 185                 190
Thr Gly Thr Pro His Tyr Met Ser Pro Glu Ala Leu Lys His Gln Gly
                195                 200                 205
Tyr Asp Thr Lys Ser Asp Ile Trp Ser Leu Ala Cys Ile Leu Tyr Glu
        210                 215                 220
Met Cys Cys Met Asn His Ala Phe Ala Gly Ser Asn Phe Leu Ser Ile
225                 230                 235                 240
Val Leu Lys Ile Val Glu Gly Asp Thr Pro Ser Leu Pro Glu Arg Tyr
                245                 250                 255
Pro Lys Glu Leu Asn Ala Ile Met Glu Ser Met Leu Asn Lys Asn Pro
                260                 265                 270
Ser Leu Arg Pro Ser Ala Ile Glu Ile Leu Lys Ile Pro Tyr Leu Asp
                275                 280                 285
Glu Gln Leu Gln Asn Leu Met Cys Arg Tyr Ser Glu Met Thr Leu Glu
        290                 295                 300
Asp Lys Asn Leu Asp Cys Gln Lys Glu Ala Ala His Ile Ile Asn Ala
305                 310                 315                 320
Met Gln Lys Arg Ile His Leu Gln Thr Leu Arg Ala Leu Ser Glu Val
                325                 330                 335
Gln Lys Met Thr Pro Arg Glu Arg Met Arg Leu Arg Lys Leu Gln Ala
                340                 345                 350
Ala Asp Glu Lys Ala Arg Lys Leu Lys Lys Ile Val Glu Glu Lys Tyr
                355                 360                 365
Glu Glu Asn Ser Lys Arg Met Gln Glu Leu Arg Ser Arg Asn Phe Gln
        370                 375                 380
Gln Leu Ser Val Asp Val Leu Glu Lys Thr His Leu Lys Gly Met
385                 390                 395                 400
Glu Glu Lys Glu Glu Gln Pro Glu Gly Arg Leu Ser Cys Ser Pro Gln
                405                 410                 415
Asp Glu Asp Glu Glu Arg Trp Gln Gly Arg Glu Glu Ser Asp Glu
                420                 425                 430
Pro Thr Leu Glu Asn Leu Pro Glu Ser Gln Pro Ile Pro Ser Met Asp
                435                 440                 445
Leu His Glu Leu Glu Ser Ile Val Glu Asp Ala Thr Ser Asp Leu Gly
        450                 455                 460
Tyr His Glu Ile Pro Glu Asp Pro Leu Val Ala Glu Tyr Tyr Ala
465                 470                 475                 480
Asp Ala Phe Asp Ser Tyr Cys Val Glu Ser Asp Glu Glu Glu
                485                 490                 495
Ile Ala Leu Glu Arg Pro Glu Lys Glu Ile Arg Asn Glu Gly Ser Gln
                500                 505                 510
Pro Ala Tyr Arg Thr Asn Gln Gln Asp Ser Asp Ile Glu Ala Leu Ala
        515                 520                 525
Arg Cys Leu Glu Asn Val Leu Gly Cys Thr Ser Leu Asp Thr Lys Thr
530                 535                 540
```

```
Ile Thr Thr Met Ala Glu Asp Met Ser Pro Gly Pro Pro Ile Phe Asn
545                 550                 555                 560

Ser Val Met Ala Arg Thr Lys Met Lys Arg Met Arg Glu Ser Ala Met
                565                 570                 575

Gln Lys Leu Gly Thr Glu Val Phe Glu Val Tyr Asn Tyr Leu Lys
            580                 585                 590

Arg Ala Arg His Gln Asn Ala Ser Glu Ala Glu Ile Arg Glu Cys Leu
                595                 600                 605

Glu Lys Val Val Pro Gln Ala Ser Asp Cys Phe Glu Val Asp Gln Leu
            610                 615                 620

Leu Tyr Phe Glu Glu Gln Leu Leu Ile Thr Met Gly Lys Glu Pro Thr
625                 630                 635                 640

Leu Gln Asn His Leu
            645
```

<210> SEQ ID NO 3
<211> LENGTH: 1449
<212> TYPE: DNA
<213> ORGANISM: homo sapiens

<400> SEQUENCE: 3

```
atgctgaaat tccaagaggc agctaagtgt gtgagtggat caacagccat ttccacttat      60
ccaaagacct tgattgcaag aagatacgtg cttcaacaaa aacttggcag tggaagtttt     120
ggaactgtct atctggtttc agacaagaaa gccaacgag gagaggaatt aaaggtactt      180
aaggaaatat ctgttggaga actaaatcca atgaaactg tacaggccaa tttggaagcc      240
caactcctct ccaagctgga ccacccagcc attgtcaagt ccatgcaagt ttttgtggag     300
caagataatt tctgcattat cacggagtac tgtgagggcc gagatctgga cgataaaatt     360
caggaatata acaagctgg aaaaatcttt ccagaaaatc aaataataga atggtttatc     420
cagctgctgc tgggagttga ctacatgcat gagaggagga tacttcatcg agacttaaag     480
tcaaagaatg tatttctgaa aaataatctc cttaaaattg gagattttgg agtttctcga     540
cttctaatgg atcctgtga cctggccaca actttaactg gaactcccca ttatatgagt     600
cctgaggctc tgaaacacca aggctatgac acaaagtcgg acatctggtc actggcatgc     660
attttgtatg agatgtgctg catgaatcat gcattcgctg ctccaatttt cttatccatt     720
gttttaaaaa ttgttgaagg tgacacacct tctctccctg agagatatcc aaaagaacta     780
aatgccatca tggaaagcat gttgaacaag aatccttcat taagaccatc tgctatcgaa     840
atttaaaaa tccttaccct tgatgagcag ctacagaacc taatgtgtag atattcagaa     900
atgactctgg aagacaaaaa tttggattgt cagaaggagg ctgctcatat aattaatgcc     960
atgcaaaaaa ggatccacct gcagactctg agggcactgt cagaagtaca gaaaatgacg    1020
ccaagagaaa ggatgcggct gaggaagctc aggcggctg atgagaaagc caggaagctg    1080
aaaaagattg tggaagaaaa atatgaagaa atagcaaac gaatgcaaga attgagatct    1140
cggaactttc agcagctgag tgttgatgta ctccatgaaa aaacacattt aaaaggaatg    1200
gaagaaaagg aggagcaacc tgagggaaga cttcttgtt caccccagga cgaggatgaa    1260
gagaggtggc aaggcaggga agaggaatct gatgaaccaa ctttagaaa cctgcctgag    1320
tctcagccta ttccttccat ggacctccac gaacttgaat caattgtaga ggatgccaca    1380
tctgaccttg ataccatgg agactgtaat ctaatttcac tagacgaata ctggaaaaat    1440
gaaaaataa                                                             1449
```

<210> SEQ ID NO 4
<211> LENGTH: 482
<212> TYPE: PRT
<213> ORGANISM: homo sapiens

<400> SEQUENCE: 4

Met Leu Lys Phe Gln Glu Ala Ala Lys Cys Val Ser Gly Ser Thr Ala
1               5                   10                  15

Ile Ser Thr Tyr Pro Lys Thr Leu Ile Ala Arg Arg Tyr Val Leu Gln
                20                  25                  30

Gln Lys Leu Gly Ser Gly Ser Phe Gly Thr Val Tyr Leu Val Ser Asp
            35                  40                  45

Lys Lys Ala Lys Arg Gly Glu Glu Leu Lys Val Leu Lys Glu Ile Ser
50                  55                  60

Val Gly Glu Leu Asn Pro Asn Glu Thr Val Gln Ala Asn Leu Glu Ala
65                  70                  75                  80

Gln Leu Leu Ser Lys Leu Asp His Pro Ala Ile Val Lys Phe His Ala
                85                  90                  95

Ser Phe Val Glu Gln Asp Asn Phe Cys Ile Ile Thr Glu Tyr Cys Glu
            100                 105                 110

Gly Arg Asp Leu Asp Asp Lys Ile Gln Glu Tyr Lys Gln Ala Gly Lys
        115                 120                 125

Ile Phe Pro Glu Asn Gln Ile Ile Glu Trp Phe Ile Gln Leu Leu Leu
    130                 135                 140

Gly Val Asp Tyr Met His Glu Arg Arg Ile Leu His Arg Asp Leu Lys
145                 150                 155                 160

Ser Lys Asn Val Phe Leu Lys Asn Asn Leu Leu Lys Ile Gly Asp Phe
                165                 170                 175

Gly Val Ser Arg Leu Leu Met Gly Ser Cys Asp Leu Ala Thr Thr Leu
            180                 185                 190

Thr Gly Thr Pro His Tyr Met Ser Pro Glu Ala Leu Lys His Gln Gly
        195                 200                 205

Tyr Asp Thr Lys Ser Asp Ile Trp Ser Leu Ala Cys Ile Leu Tyr Glu
    210                 215                 220

Met Cys Cys Met Asn His Ala Phe Ala Gly Ser Asn Phe Leu Ser Ile
225                 230                 235                 240

Val Leu Lys Ile Val Glu Gly Asp Thr Pro Ser Leu Pro Glu Arg Tyr
                245                 250                 255

Pro Lys Glu Leu Asn Ala Ile Met Glu Ser Met Leu Asn Lys Asn Pro
            260                 265                 270

Ser Leu Arg Pro Ser Ala Ile Glu Ile Leu Lys Ile Pro Tyr Leu Asp
        275                 280                 285

Glu Gln Leu Gln Asn Leu Met Cys Arg Tyr Ser Glu Met Thr Leu Glu
    290                 295                 300

Asp Lys Asn Leu Asp Cys Gln Lys Glu Ala His Ile Ile Asn Ala
305                 310                 315                 320

Met Gln Lys Arg Ile His Leu Gln Thr Leu Arg Ala Leu Ser Glu Val
                325                 330                 335

Gln Lys Met Thr Pro Arg Glu Arg Met Arg Leu Arg Lys Leu Gln Ala
            340                 345                 350

Ala Asp Glu Lys Ala Arg Lys Leu Lys Ile Val Glu Glu Lys Tyr
        355                 360                 365

Glu Glu Asn Ser Lys Arg Met Gln Glu Leu Arg Ser Arg Asn Phe Gln

|    |     |     |     |     |     |     |     |     |     |     |     |     |
|----|-----|-----|-----|-----|-----|-----|-----|-----|-----|-----|-----|-----|
|    | 370 |     |     |     | 375 |     |     |     | 380 |     |     |     |
| Gln | Leu | Ser | Val | Asp | Val | Leu | His | Glu | Lys | Thr | His | Leu | Lys | Gly | Met |
| 385 |     |     |     |     | 390 |     |     |     |     | 395 |     |     |     |     | 400 |

Gln Leu Ser Val Asp Val Leu His Glu Lys Thr His Leu Lys Gly Met
385                     390                     395                     400

Glu Glu Lys Glu Glu Gln Pro Glu Gly Arg Leu Ser Cys Ser Pro Gln
            405                     410                     415

Asp Glu Asp Glu Glu Arg Trp Gln Gly Arg Glu Glu Ser Asp Glu
            420                     425                     430

Pro Thr Leu Glu Asn Leu Pro Glu Ser Gln Pro Ile Pro Ser Met Asp
                435                     440                     445

Leu His Glu Leu Glu Ser Ile Val Glu Asp Ala Thr Ser Asp Leu Gly
        450                     455                     460

Tyr His Gly Asp Cys Asn Leu Ile Ser Leu Asp Glu Tyr Trp Lys Asn
465                     470                     475                     480

Glu Lys

<210> SEQ ID NO 5
<211> LENGTH: 2847
<212> TYPE: DNA
<213> ORGANISM: homo sapiens

<400> SEQUENCE: 5

| | | | | | |
|---|---|---|---|---|---|
| ccgcgccgtc | tccctggcca | cggttccaaa | cagccgtggc | ccgcggtgtc | tggcgctcgg | 60 |
| tgggtgtggt | tgcccctagt | ttgaggcctg | cccgattacc | cgcaagactt | gggcagcccc | 120 |
| gggcgccgct | ccgaccacga | cagggaaagg | aaccttaatc | tcatctttaa | aataaggaga | 180 |
| attactgagt | gacctgaagg | accctttttca | gctggaaagt | ctgaactgac | caacactgga | 240 |
| tgaatttgac | catttcttag | gagactggaa | tgttaagttt | ctataaatga | atgaaccagt | 300 |
| tctctcttgt | ttggagcaat | gctgaaattc | caagaggcag | ctaagtgtgt | gagtggatca | 360 |
| acagccattt | ccacttatcc | aaagaccttg | attgcaagaa | gatacgtgct | tcaacaaaaa | 420 |
| cttggcagtg | aagttttgg | aactgtctat | ctggtttcag | acaagaaagc | caaacgagga | 480 |
| gaggaattaa | aggtacttaa | ggaaatatct | gttggagaac | taaatccaaa | tgaaactgta | 540 |
| caggccaatt | tggaagccca | actcctctcc | aagctggacc | acccagccat | tgtcaagttc | 600 |
| catgcaagtt | ttgtggagca | agataatttc | tgcattatca | cggagtactg | tgagggccga | 660 |
| gatctggacg | ataaaattca | ggaatataaa | caagctggaa | aaatctttcc | agaaaatcaa | 720 |
| ataatagaat | ggtttatcca | gctgctgctg | ggagttgact | acatgcatga | gaggaggata | 780 |
| cttcatcgag | acttaaagtc | aaagaatgta | tttctgaaaa | ataatctcct | taaaattgga | 840 |
| gattttggag | tttctcgact | tctaatggga | tcctgtgacc | tggccacaac | tttaactgga | 900 |
| actccccatt | atatgagtcc | tgaggctctg | aaacaccaag | gctatgacac | aaagtcggac | 960 |
| atctggtcac | tggcatgcat | tttgtatgag | atgtgctgca | tgaatcatgc | attcgctggc | 1020 |
| tccaatttct | tatccattgt | tttaaaaatt | gttgaaggtg | acacaccttc | tctccctgag | 1080 |
| agatatccaa | agaactaaa | tgccatcatg | gaaagcatgt | tgaacaagaa | tccttcatta | 1140 |
| agaccatctg | ctatcgaaat | tttaaaaatc | ccttaccttg | atgagcagct | acagaaccta | 1200 |
| atgtgtagat | attcagaaat | gactctggaa | gacaaaaatt | tggattgtca | gaaggaggct | 1260 |
| gctcatataa | ttaatgccat | gcaaaaaagg | atccacctgc | agactctgag | ggcactgtca | 1320 |
| gaagtacaga | aaatgacgcc | aagagaaagg | atgcggctga | ggaagctcca | ggcggctgat | 1380 |
| gagaaagcca | ggaagctgaa | aaagattgtg | aagaaaaat | atgaagaaaa | tagcaaacga | 1440 |
| atgcaagaat | tgagatctcg | gaactttcag | cagctgagtg | ttgatgtact | ccatgaaaaa | 1500 |

```
acacatttaa aaggaatgga agaaaaggag gagcaacctg agggaagact ttcttgttca    1560
ccccaggacg aggatgaaga gaggtggcaa ggcagggaag aggaatctga tgaaccaact    1620
ttagagaacc tgcctgagtc tcagcctatt ccttccatgg acctccacga acttgaatca    1680
attgtagagg atgccacatc tgaccttgga taccatgaga tcccagaaga cccacttgtg    1740
gctgaagagt actacgctga tgcatttgat tcctattgtg tagagagtga tgaggaggaa    1800
gaagaaatag cgttagaaag accagagaaa gaaatcagga atgagggatc ccagcctgct    1860
tacagaacaa accaacagga cagtgatatc gaagcgttgg ccaggtgttt ggaaaatgtc    1920
ctgggttgca cttctctaga cacaaagacc atcaccacca tggctgaaga catgtcccca    1980
ggaccaccaa ttttcaacag tgtgatggcc aggaccaaga tgaaacgcat gagggaatca    2040
gccatgcaga agctggggac agaagtattt gaagaggtct ataattacct caagagagca    2100
aggcatcaga atgctagcga agcagagatc cgcgagtgtt tggaaaaagt ggtgcctcaa    2160
gccagcgact gttttgaagt ggaccagctc ctgtactttg aagagcagtt gctgatcacg    2220
atgggaaaag aacctactct ccagaaccat ctctaggcaa ctatcaaaaa gaagcagaag    2280
ttcaagtgga caaatttatg tgaaaattca tttaacatat aagctgaact ctattatggg    2340
gaatggatac aaaagcagag ctcccatctt gactttcaat tcctcatcag aagtactggc    2400
ttctttagag agtagtaagc atggctgcct atgcttggag tcataagtgt tatttggact    2460
ataccctgag ataagcttat agatcaagtt tggctccctt gaaaagcatt tctctcatgt    2520
gcgccctcag ggcttccagc aggattgagt caccctgacg atgaccggga gaagccgtgt    2580
gctcttcatt attttcagct ggaggacaga gctcagtgcc tgactgccta gggtctcatg    2640
gactgtaggc agcctgccag tgaaggtcac tggactctag cctacaacat gctgagctac    2700
agcccagaag ccagacatgc ctgtcttagc tgacctgttt ttggtccact tttgcccttc    2760
catgactaat aaggaagata tgtgtgtatt tcatacacac acaaggacct ggattaaaaa    2820
tccaaaaagt gaaaaaaaaa aaaaaaa                                       2847
```

HUMAN KINASES AND POLYNUCLEOTIDES ENCODING THE SAME

The present application claims the benefit of U.S. Provisional Application Ser. No. 60/293,248, which was filed on May 24, 2001, and is herein incorporated by reference in its entirety.

1. INTRODUCTION

The present invention relates to the discovery, identification, and characterization of novel human polynucleotides encoding proteins sharing sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over-express the disclosed polynucleotides, antagonists and agonists of the proteins, and other compounds that modulate the expression or activity of the proteins encoded by the disclosed polynucleotides, which can be used for diagnosis, drug screening, clinical trial monitoring, the treatment of diseases and disorders, and cosmetic or nutriceutical applications.

2. BACKGROUND OF THE INVENTION

Kinases mediate the phosphorylation of a wide variety of proteins and compounds in the cell. Along with phosphatases, kinases are involved in a range of regulatory pathways. Given the physiological importance of kinases, they have been subject to intense scrutiny and are proven drug targets.

3. SUMMARY OF THE INVENTION

The present invention relates to the discovery, identification, and characterization of nucleotides that encode novel human proteins, and the corresponding amino acid sequences of these proteins. The novel human proteins (NHPS) described for the first time herein share structural similarity with animal kinases, including, but not limited to, serine-threonine kinases and G2 protein kinases. Accordingly, the described NHPs encode novel kinases having homologues and orthologs across a range of phyla and species.

The novel human polynucleotides described herein encode open reading frames (ORFs) encoding proteins of 645 and 482 amino acids in length (see, respectively, SEQ ID NOS:2 and 4).

The invention also encompasses agonists and antagonists of the described NHPs, including small molecules, large molecules, mutant NHPs, or portions thereof, that compete with native NHPs, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-outs" (which can be conditional) that do not express a functional NHP. Knock-out mice can be produced in several ways, one of which involves the use of mouse embryonic stem cell ("ES cell") lines that contain gene trap mutations in a murine homolog of at least one of the described NHPs. When the unique NHP sequences described in SEQ ID NOS:1–5 are "knocked-out" they provide a method of identifying phenotypic expression of the particular gene, as well as a method of assigning function to previously unknown genes. In addition, animals in which the unique NHP sequences described in SEQ ID NOS:1–5 are "knocked-out" provide a unique source in which to elicit antibodies to homologous and orthologous proteins, which would have been previously viewed by the immune system as "self" and therefore would have failed to elicit significant antibody responses.

Additionally, the unique NHP sequences described in SEQ ID NOS:1–5 are useful for the identification of protein coding sequences, and mapping a unique gene to a particular chromosome. These sequences identify biologically verified exon splice junctions, as opposed to splice junctions that may have been bioinformatically predicted from genomic sequence alone. The sequences of the present invention are also useful as additional DNA markers for restriction fragment length polymorphism (RFLP) analysis, and in forensic biology, particularly given the presence of nucleotide-polymorphisms within the described sequences.

Further, the present invention also relates to processes for identifying compounds that modulate, i.e., act as agonists or antagonists of, NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequence of the novel human ORFs encoding the described novel human kinase proteins. SEQ ID NO:5 describes a NHP ORF and flanking sequences.

5. DETAILED DESCRIPTION OF THE INVENTION

The NHPs described for the first time herein are novel proteins that are expressed in, inter alia, human cell lines and human fetal brain, brain, pituitary, lung, kidney, lymph node, testis, thyroid, adrenal gland, fetal kidney, fetal lung and osteosarcoma cells. The described sequences were compiled from sequences available in GENBANK, and cDNAs generated from human lymph node, brain, fetal brain, thyroid, and testis mRNAs (Edge Biosystems, Gaithersburg, Md.) that were identified using primers generated from human genomic DNA.

The present invention encompasses the nucleotides presented in the Sequence Listing, host cells expressing such nucleotides, the expression products of such nucleotides, and: (a) nucleotides that encode mammalian homologs of the described nucleotides, including the specifically described NHPs, and the NHP products; (b) nucleotides that encode one or more portions of a NHP that correspond to functional domains, and the polypeptide products specified by such nucleotide sequences, including, but not limited to, the novel regions of any active domain(s); (c) isolated nucleotides that encode mutant versions, engineered or naturally occurring, of the described NHPs, in which all or a part of at least one domain is deleted or altered, and the polypeptide products specified by such nucleotide sequences, including, but not limited to, soluble proteins and peptides; (d) nucleotides that encode chimeric fusion proteins containing all or a portion of a coding region of a NHP, or one of its domains (e.g., a receptor/ligand binding domain, accessory protein/self-association domain, etc.) fused to another peptide or polypeptide; or (e) therapeutic or diagnostic derivatives of the described polynucleotides, such as oligonucleotides, antisense polynucleotides, ribozymes, dsRNA, or gene therapy constructs, comprising a sequence first disclosed in the Sequence Listing.

As discussed above, the present invention includes the human DNA sequences presented in the Sequence Listing (and vectors comprising the same), and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & Sons, Inc., N.Y., at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHP product. Functional equivalents of a NHP include naturally occurring NHPs present in other species, and mutant NHPs, whether naturally occurring or engineered (by site directed mutagenesis, gene shuffling, directed evolution as described in, for example, U.S. Pat. Nos. 5,837,458 or 5,723,323 both of which are herein incorporated by reference). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar to corresponding regions of SEQ ID NOS:1 or 3 (as measured by BLAST sequence comparison analysis using, for example, the GCG sequence analysis package, as described herein, using default parameters).

The invention also includes nucleic acid molecules, preferably DNA molecules, that hybridize to, and are therefore the complements of, the described NHP-encoding polynucleotides. Such hybridization conditions can be highly stringent or less highly stringent, as described herein. In instances where the nucleic acid molecules are deoxyoligonucleotides ("DNA oligos"), such molecules are generally about 16 to about 100 bases long, or about 20 to about 80 bases long, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a microarray or high-throughput "chip" format). Additionally, a series of NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS:1–5 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS:1–5, or an amino acid sequence encoded thereby. Methods for attaching biopolymers to, or synthesizing biopolymers on, solid support matrices, and conducting binding studies thereon, are disclosed in, inter alia, U.S. Pat. Nos. 5,700,637, 5,556,752, 5,744,305, 4,631,211, 5,445, 934, 5,252,743, 4,713,326, 5,424,186, and 4,689,405, the disclosures of which are herein incorporated by reference in their entirety.

Addressable arrays comprising sequences first disclosed in SEQ ID NOS:1–5 can be used to identify and characterize the temporal and tissue specific expression of a gene. These addressable arrays incorporate oligonucleotide sequences of sufficient length to confer the required specificity, yet be within the limitations of the production technology. The length of these probes is usually within a range of between about 8 to about 2000 nucleotides. Preferably the probes consist of 60 nucleotides, and more preferably 25 nucleotides, from the sequences first disclosed in SEQ ID NOS:1–5.

For example, a series of NHP oligonucleotide sequences, or the complements thereof, can be used in chip format to represent all or a portion of the described sequences. The oligonucleotides, typically between about 16 to about 40 (or any whole number within the stated range) nucleotides in length, can partially overlap each other, and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing, and proceed in either a sense (5'-to-3') orientation vis-a-vis the described sequence or in an antisense orientation.

Microarray-based analysis allows the discovery of broad patterns of genetic activity, providing new understanding of gene functions, and generating novel and unexpected insight into transcriptional processes and biological mechanisms. The use of addressable arrays comprising sequences first disclosed in SEQ ID NOS:1–5 provides detailed information about transcriptional changes involved in a specific pathway, potentially leading to the identification of novel components, or gene functions that manifest themselves as novel phenotypes.

Probes consisting of sequences first disclosed in SEQ ID. NOS:1–5 can also be used in the identification, selection, and validation of novel molecular targets for drug discovery. The use of these unique sequences permits the direct confirmation of drug targets, and recognition of drug dependent changes in gene expression that are modulated through pathways distinct from the intended target of the drug. These unique sequences therefore also have utility in defining and monitoring both drug action and toxicity.

As an example of utility, the sequences first disclosed in SEQ ID NOS:1–5 can be utilized in microarrays, or other assay formats, to screen collections of genetic material from patients who have a particular medical condition. These investigations can also be carried out using the sequences first disclosed in SEQ ID NOS:1–5 in silico, and by comparing previously collected genetic databases and the disclosed sequences using computer software known to those in the art.

Thus the sequences first disclosed in SEQ ID NOS:1–5 can be used to identify mutations associated with a particular disease, and also in diagnostic or prognostic assays.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence, in conjunction with the presence of one or more specific oligonucleotide sequence(s) first disclosed in SEQ ID NOS:1–5. Alternatively, a restriction map specifying the relative positions of restriction endonuclease digestion sites, or various palindromic or other specific oligonucleotide sequences, can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP antisense molecules, useful, for example, in NHP gene regulation and/or as antisense primers in amplification reactions of NHP nucleic acid sequences. With respect to NHP gene regulation, such techniques can be used to regulate biological functions. Further, such sequences can be used as part of ribozyme and/or triple helix sequences that are also useful for NHP gene regulation.

Inhibitory antisense or double stranded oligonucleotides can additionally comprise at least one modified base moiety that is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-inethoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g.,. by use of an automated DNA synthesizer (such as are commercially available from Biosearch, Applied Biosystems, etc.). As examples, phosphorothidate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. USA 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Spring Harbor Press, Cold Spring Harbor, N.Y. (and periodic updates thereof), and Ausubel et al., 1989, supra.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

For example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHP gene homolog can be isolated from nucleic acid from an organism of interest by performing PCR using two degenerate or "wobble oligonucleotide primer pools designed on the basis of amino acid sequences within the NHP products disclosed herein. The template for the reaction may be total RNA, mRNA, genomic DNA and/or cDNA obtained by reverse transcription of mRNA prepared from, for example, human or non-human cell lines or tissue known to express, or suspected of expressing, an allele of a NHP gene.

The PCR product can be subcloned and sequenced to ensure that the amplified sequences represent the sequence of the desired NHP gene. The PCR fragment can then be used to isolate a full length CDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known to express, or suspected of expressing, a NHP gene). A reverse transcription (RT) reaction can be performed on the RNA using an oligonucleotide primer specific for the most 5' end of the amplified fragment for the priming of first strand synthesis. The resulting RNA/DNA hybrid may then be tailed" using a standard terminal transferase reaction, the hybrid may be digested with RNase H, and second strand synthesis may then be primed with a complementary primer. Thus, CDNA sequences upstream of the amplified fragment can be isolated. For a review of cloning strategies that can be used, see, e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to MRNA isolated from tissue known to express, or suspected of expressing, a NHP, in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHP allele to that of a corresponding normal NHP allele, the mutation (s) responsible for the loss or alteration of function of the mutant NHP gene product can be ascertained.

Alternatively, a genomic library can be constructed using DNA obtained from an individual suspected of carrying, or known to carry, a mutant NHP allele (e.g., a person manifesting a NHP-associated phenotype such as, for example, behavioral disorders, immune disorders, obesity, high blood pressure, etc.), or a cDNA library can be constructed using PNA from a tissue known to express, or suspected of expressing, a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well-known to those skilled in the art.

Additionally, an expression library can be constructed utilizing cDNA synthesized from, for example, RNA isolated from a tissue known to express, or suspected of expressing, a mutant NHP allele in an individual suspected of carrying, or known to carry, such a mutant allele. In this manner, gene products made by the putatively mutant tissue may be expressed and screened using standard antibody screening techniques in conjunction with antibodies raised against a normal NHP product, as described below (for screening techniques, see, for example, Harlow and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to a NHP are likely to cross-react with a corresponding mutant NHP expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323, which are herein incorporated by reference in their entirety.

The invention also encompasses: (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869, 336, herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators, and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 or adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast a-mating factors.

Where, as in the present instance, some of the described NHP peptides or polypeptides are thought to be cytoplasmic or nuclear proteins (although processed forms or fragments can be secreted or membrane associated), expression systems can be engineered that produce soluble derivatives of a NHP (corresponding to a NHP extracellular and/or intracellular domains, or truncated polypeptides lacking one or more hydrophobic domains) and/or NHP fusion protein products (especially NHP-Ig fusion proteins, i.e., fusions of a NHP domain to an IgFc), NHP antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHP, as well as compounds or nucleotide constructs that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs, or inappropriately expressed NHPs, for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHP in the body. The use of engineered host cells and/or animals can offer an advantage in that such systems allow not only for the identification of compounds that bind to the endogenous receptor/ligand of a NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of a soluble NHP, a NHP-IgFc fusion protein, or an anti-idiotypic antibody (or its Fab) that mimics the NHP, could activate or effectively antagonize the endogenous NHP or a protein interactive therewith. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules, can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The NHP Sequences

The cDNA sequences and corresponding deduced amino acid sequences of the described NHPs are presented in the Sequence Listing.

Expression analysis has provided evidence that the described NHPs can be expressed in a relatively narrow range of human tissues. In addition to serine-threonine kinases, the described NHPs also share significant similarity to a range of additional kinase families, including kinases associated with signal transduction, from a variety of phyla and species. An A/G polymorphism was identified at the region represented by nucleotide position number 350 of, for example, SEQ ID NO:1 or SEQ ID NO:3, which can result in an asp or gly being present at corresponding amino acid (aa) position 117 of, for example, SEQ ID NO:2 or SEQ ID NO:4; and a T/A polymorphism was identified at the region represented by nucleotide position number 1463 of, for example, SEQ ID NO:1, which can result in a val or glu being present at corresponding aa position 488 of, for example, SEQ ID NO:2. The present invention contemplates sequences comprising any and all combinations and permutations of the above polymorphisms. As these polymorphisms are coding single nucleotide polymorphisms, they are particularly useful in forensic analysis.

The gene encoding the described NHPs is apparently encoded on human chromosome 3 (see GENBANK accession no. AC010210). Accordingly, the described sequences are also useful for mapping and identifying the coding regions of the human genome, and for defining exon splice junctions.

Given the physiological importance of protein kinases, they have been subject to intense scrutiny, as exemplified and discussed in U.S. Pat. Nos. 5,756,289 and 5,817,479, and 6,340,583, herein incorporated by reference in their entirety, which additionally describe a variety of uses and applications for the described NHPs.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees, may be used to generate NHP transgenic animals.

Any technique known in the art may be used to introduce a NHP transgene into animals to produce the founder lines of transgenic animals. Such techniques include, but are not limited to, pronuclear microinjection (Hoppe and Wagner, 1989, U.S. Pat. No. 4,873,191); retrovirus-mediated gene transfer into germ lines (Van der Putten et al., 1985, Proc. Natl. Acad. Sci. USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 19 LEX-0348-USA 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry a NHP transgene in all their cells, as well as animals that carry a transgene in some, but not all their cells, i.e., mosaic animals or somatic cell transgenic animals. A transgene may be integrated as a single transgene, or in concatamers, e.g., head-to-head tandems or head-to-tail tandems. A transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell-type, thus inactivating the endogenous NHP gene in only that cell-type, by following, for example, the teaching of Gu et al., 1994, Science 265:103–106. The regulatory sequences required for such a cell-type specific inactivation will depend upon the particular cell-type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of NHP gene-expressing tissue may also be evaluated immunocytochemically using antibodies specific for the NHP transgene product.

The present invention also provides for "knock-in" animals. Knock-in animals are those in which a polynucleotide sequence (i.e., a gene or a CDNA) that the animal does not naturally have in its genome is inserted in such a way that it is expressed. Examples include, but are not limited to, a human gene or cDNA used to replace its murine ortholog in the mouse, a murine CDNA used to replace the murine gene in the mouse, and a human gene or cDNA or murine cDNA that is tagged with a reporter construct used to replace the murine ortholog or gene in the mouse. Such replacements can occur at the locus of the murine ortholog or gene, or at another specific site. Such knock-in animals are useful for the in vivo study, testing and validation of, intra alia, human drug targets, as well as for compounds that are directed at the same, and therapeutic proteins.

5.2 NHPS and NHP Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, and as reagents in assays for screening for compounds that can be used as pharmaceutical reagents useful in the therapeutic treatment of mental, biological, or medical disorders and diseases. Given the similarity information and expression data, the described NHPs can be targeted (by drugs, oligos, antibodies, etc.) in order to treat disease, or to therapeutically augment the efficacy of therapeutic agents.

The Sequence Listing discloses the amino acid sequences encoded by the described NHP-encoding polynucleotides. The NHPs display initiator methionines that are present in DNA sequence contexts consistent with eucaryotic translation initiation sites. The NHPs do not display signal-like sequences, which indicates that they may not be membrane associated, and are possibly cytoplasmic or nuclear proteins, although they may also be secreted proteins.

The NHP amino acid sequences of the invention include the amino acid sequences presented in the Sequence Listing, as well as analogues and derivatives thereof. Further, corresponding NHP homologues from other species are encompassed by the invention. In fact, any NHP protein encoded by the NHP nucleotide sequences described herein are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al., eds., Scientific American Books, New York, N.Y., herein incorporated by reference), are generically representative of all the various permutations and combinations of nucleic acid sequences that can encode such amino acid sequences.

The invention also encompasses proteins that are functionally equivalent to the NHPs encoded by the presently described nucleotide sequences, as judged by any of a number of criteria, including, but not limited to, the ability to bind and modify a NHP substrate, the ability to effect an identical or complementary downstream pathway, or a change in cellular metabolism (e.g., proteolytic activity, ion flux, phosphorylation, etc.). Such functionally equivalent NHP proteins include, but are not limited to, additions or substitutions of amino acid residues within the amino acid sequence encoded by the NHP nucleotide sequences described herein, but that result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where the NHP peptide or polypeptide can exist, or has been engineered to exist, as a soluble or secreted molecule, the soluble NHP peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well-known to those skilled in the art. However, such engineered host cells themselves may be used in situations where it is important not only to retain the structural and functional characteristics of a NHP, but to assess biological activity, e.g., in certain drug screening assays.

The expression systems that may be used for purposes of the invention include, but are not limited to, microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing NHP nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing a NHP, or for raising antibodies to a NHP, vectors that direct the expression of high levels of fusion protein products that are readily purified may be desirable. Such vectors include, but are not limited to, the *E. coli* expression vector pUR278 (Ruther et al., 1983, EMBO J. 2:1791), in which a NHP coding sequence may be ligated individually into the vector in-frame with the lacZ coding region so that a fusion protein is produced; pIN vectors (Inouye and Inouye, 1985, Nucleic Acids Res. 13:3101–3109; Van Heeke and Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target expression product can be released from the GST moiety.

In an exemplary insect system, *Autographa californica* nuclear polyhedrosis virus (AcNPV) is used as a vector to express foreign polynucleotide sequences. The virus grows in *Spodoptera frugiperda* cells. A NHP coding sequence can be cloned individually into a non-essential region (for example the polyhedrin gene) of the virus and placed under control of an AcNPV promoter (for example the polyhedrin promoter). Successful insertion of a NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., see Logan and Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, may be provided. Furthermore, the initiation codon should be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al.,. 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the desired modification and processing of the foreign protein expressed. To this end, eukaryotic host cells that possess the. cellular machinery for the desired processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the a product. Such engineered cell lines may be particularly useful in screening and evaluation of compounds that affect the endogenous activity of a NHP product.

A number of selection systems may be used, including, but not limited to, the herpes simplex virus thymidine kinase (Wigler et al., 1977, Cell 11:223), hypoxanthine-guanine phosphoribosyltransferase (Szybalska and Szybalski, 1962, Proc. Natl. Acad. Sci. USA 48:2026), and adenine phosphoribosyltransferase (Lowy et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, Proc. Natl. Acad. Sci. USA 77:3567; O'Hare et al., 1981, Proc. Natl. Acad. Sci. USA 78:1527); gpt, which confers resistance to mycophenolic acid (Mulligan and Berg, 1981, Proc. Natl. Acad. Sci. USA 78:2072); neo, which confers resistance to the aminoglycoside G-418 (Colberre-Garapin et al., 1981, J. Mol. Biol. 150:1); and-hygro, which confers resistance to hygromycin (Santerre et al., 1984, Gene 30:147).

Alternatively, any fusion protein can be readily purified by utilizing an antibody specific for the fusion protein being expressed. Another exemplary system allows for the ready purification of non-denatured fusion proteins expressed in human cell lines (Janknecht et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Also encompassed by the present invention are fusion proteins that direct a NHP to a target organ and/or facilitate transport across the membrane into the cytosol. Conjugation of NHPs to antibody molecules or their Fab fragments could be used to target cells bearing a particular epitope. Attaching an appropriate signal sequence to a NHP would also transport a NHP to a desired location within the cell. Alternatively targeting of a NHP or its nucleic acid sequence might be achieved using liposome or lipid complex based delivery systems. Such technologies are described in "Liposomes: A Practical Approach", New, R.R.C., ed., Oxford University Press, N.Y., and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of NHPs to a target site or desired organ, where they cross the cell membrane and/or the nucleus where the NHPs can exert their functional activity. This goal may be achieved by coupling of a NHP to a cytokine or other ligand that provides targeting specificity, and/or to a protein transducing domain (see generally U.S. Provisional Patent Application Ser. Nos. 60/111,701 and 60/056,713, both of which are herein incorporated by reference, for examples of such transducing sequences), to facilitate passage across cellular membranes, and can optionally be engineered to include nuclear localization signals.

Additionally contemplated are oligopeptides that are modeled on an amino acid sequence first described in the Sequence Listing. Such NHP oligopeptides are generally between about 10 to about 100 amino acids long, or between about 16 to about 80 amino acids long, or between about 20 to about 35 amino acids long, or any variation or combination of sizes represented therein that incorporate a contiguous region of sequence first disclosed in the Sequence Listing. Such NHP oligopeptides can be of any length disclosed within the above ranges and can initiate at any amino acid position represented in the Sequence Listing.

The invention also contemplates "substantially isolated" or "substantially pure" proteins or polypeptides. By a "substantially isolated" or "substantially pure" protein or polypeptide is meant a protein or polypeptide that has been separated from at least some of those components that naturally accompany it. Typically, the protein or polypeptide is substantially isolated or pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially isolated or pure protein or polypeptide may be obtained, for example, by extraction from a natural source, by expression of a recombinant nucleic acid encoding the protein or polypeptide, or by chemically synthesizing the protein or polypeptide.

Purity can be measured by any appropriate method, e.g., column chromatography such as immunoaffinity chromatography using an antibody specific for the protein or polypeptide, polyacrylamide gel electrophoresis, or HPLC analysis. A protein or polypeptide is substantially free of naturally associated components when it is separated from at least some of those contaminants that accompany it in its natural state. Thus, a polypeptide that is chemically synthesized or produced in a cellular system different from the cell from which it naturally originates will be, by definition, substantially free from its naturally associated components. Accordingly, substantially isolated or pure proteins or polypeptides include eukaryotic proteins synthesized in *E. coli*, other prokaryotes, or any other organism in which they do not naturally occur.

5.3 Antibodies to NHP Products

Antibodies that specifically recognize one or more epitopes of a NHP, epitopes of conserved variants of a NHP, or peptide fragments of a NHP, are also encompassed by the invention. Such antibodies include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of a NHP in a biological sample and may, therefore, be utilized as part of a diagnostic or prognostic technique whereby patients may be tested for abnormal amounts of a NHP. Such antibodies may also be utilized in conjunction with, for example, compound screening schemes for the evaluation of the effect of test compounds on expression and/or activity of a NHP expression product. Additionally, such antibodies can be used in conjunction with gene therapy to, for example, evaluate normal and/or engineered NHP-expressing cells prior to their introduction into a patient. Such antibodies may additionally be used in methods for the inhibition of abnormal NHP activity. Thus, such antibodies may be utilized as a part of treatment methods.

For the production of antibodies, various host animals may be immunized by injection with a NHP, a NHP peptide (e.g., one corresponding to a functional domain of a NHP), a truncated NHP polypeptide (a NHP in which one or more domains have been deleted), functional equivalents of a NHP or mutated variants of a NHP. Such host animals may include, but are not limited to, pigs, rabbits, mice, goats, and rats, to name but a few. Various adjuvants may be used to increase the immunological response, depending on the host species, including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and/or coupling with molecules such as keyhole limpet hemocyanin, tetanus toxoid, diphtheria toxoid, ,ovalbumin, cholera toxin, or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class, including IgG, IgM, IgE, IgA, and IgD, and any subclass thereof. The hybridomas producing the mAbs of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,114,598, 6,075,181 and 5,877,397 and their respective disclosures, which are herein incorporated by reference in their entirety. Also encompassed by the present invention is the use of fully humanized monoclonal antibodies, as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: F(ab')$_2$ fragments, which can be produced by pepsin digestion of an antibody molecule; and Fab fragments, which can be generated by reducing the disulfide bridges of F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well-known to those skilled in the art (see, e.g., Greenspan and Bona, 1993, FASEB J. 7:437–444; and Nissinoff, 1991, J. Immunol. 147:2429–2438). For example, antibodies that bind to a NHP domain and competitively inhibit the binding of a NHP to its cognate receptor/ligand can be used to generate anti-idiotypes that "mimic" the NHP and, therefore, bind, activate, or neutralize a NHP, NHP receptor, or NHP ligand. Such anti-idiotypic antibodies, or Fab fragments of such anti-idiotypes, can be used in therapeutic regimens involving a NHP-mediated pathway.

Additionally given the high degree of relatedness of mammalian NHPs, NHP knock-out mice (having never seen a NHP, and thus never been tolerized to a NHP) have a unique utility, as they can be advantageously applied to the generation of antibodies against the disclosed mammalian NHPs (i.e., a NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are thin the scope of the appended claims. All patents, and patent applications are by reference in their entirety.

What is claimed is:

1. An isolated nucleic acid molecule comprising the nucleotide sequence of SEQ ID NO:3.

2. An isolated nucleic acid molecule comprising a nucleotide sequence encoding the amino acid sequence shown in SEQ ID NO:4.

3. A recombinant expression vector comprising a nucleic acid molecule encoding the amino acid sequence shown in SEQ ID NO:4.

4. The recombinant expression vector of claims 3, wherein said nucleic acid molecule comprises the nucleotide sequence of SEQ ID NO:3.

5. A host cell comprising the recombinant expression vector of claim 3.

* * * * *